(12) United States Patent
Murray

(10) Patent No.: US 9,884,134 B2
(45) Date of Patent: Feb. 6, 2018

(54) MACHINE FOR FORMING FLEXIBLE POUCHES

(71) Applicant: Pouch Pac Innovations LLC, Sarasota, FL (US)

(72) Inventor: R. Charles Murray, Sarasota, FL (US)

(73) Assignee: Pouch Pac Innovations, LLC, Sarasota, FL (US)

( * ) Notice: Subject to any disclaimer, the term of this patent is extended or adjusted under 35 U.S.C. 154(b) by 548 days.

(21) Appl. No.: 14/492,825

(22) Filed: Sep. 22, 2014

(65) Prior Publication Data

US 2015/0086422 A1 Mar. 26, 2015

Related U.S. Application Data

(60) Provisional application No. 61/880,363, filed on Sep. 20, 2013.

(51) Int. Cl.
*A61L 2/20* (2006.01)

(52) U.S. Cl.
CPC ........... *A61L 2/208* (2013.01); *A61L 2202/23* (2013.01); *A61L 2202/26* (2013.01)

(58) Field of Classification Search
CPC ... B65H 45/00; A61L 2/20; A61L 2/24; A61L 2/202
See application file for complete search history.

(56) References Cited

U.S. PATENT DOCUMENTS

| 6,719,015 | B2 | 4/2004 | Murray | |
|---|---|---|---|---|
| 6,744,515 | B1 * | 6/2004 | Totani | B26D 5/007 |
| | | | | 356/429 |
| 6,854,490 | B2 | 2/2005 | Murray | |
| 7,584,593 | B2 | 9/2009 | Murray | |
| 7,722,254 | B2 | 5/2010 | Murray | |
| 8,028,502 | B2 | 10/2011 | Murray | |
| 8,573,445 | B2 | 1/2013 | Murray | |
| 8,647,246 | B2 | 2/2014 | Murray | |
| 2002/0159915 | A1 * | 10/2002 | Zelina | A61L 2/208 |
| | | | | 422/28 |
| 2011/0152051 | A1 * | 6/2011 | Murray | B65B 3/04 |
| | | | | 493/213 |
| 2014/0076457 | A1 | 3/2014 | Murray | |

* cited by examiner

*Primary Examiner* — Sean E Conley
(74) *Attorney, Agent, or Firm* — Dinsmore & Shohl LLP

(57) ABSTRACT

The disclosure is directed to machines for manufacturing a flexible pouch that sterilizes the flexible pouch material, seals the fitment within the pouch, and inspects the fitment installation. A sterilization chamber in the machine a box having an oxygen supplied entry compartment, a hydrogen peroxide supplied center compartment, and an oxygen supplied exit compartment. To a secure the fitment within the flexible pouch, a seal bar including a center cavity disposed between a pair of sideways L-shaped portions is used. After the fitment is installed into the flexible pouch, it is inspected with a digital photograph analysis apparatus.

8 Claims, 8 Drawing Sheets

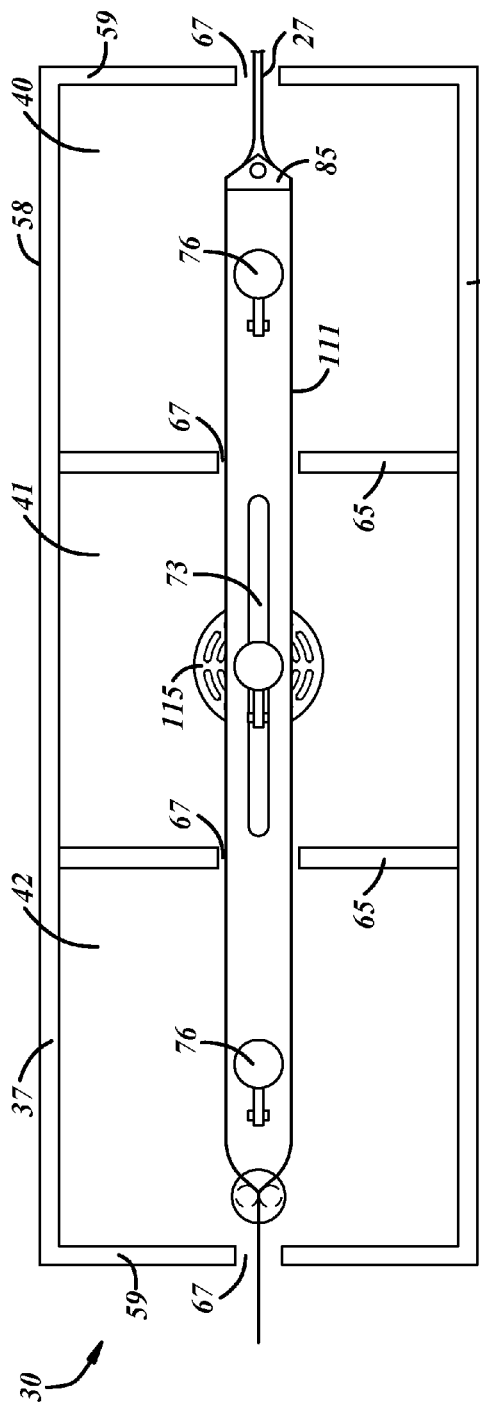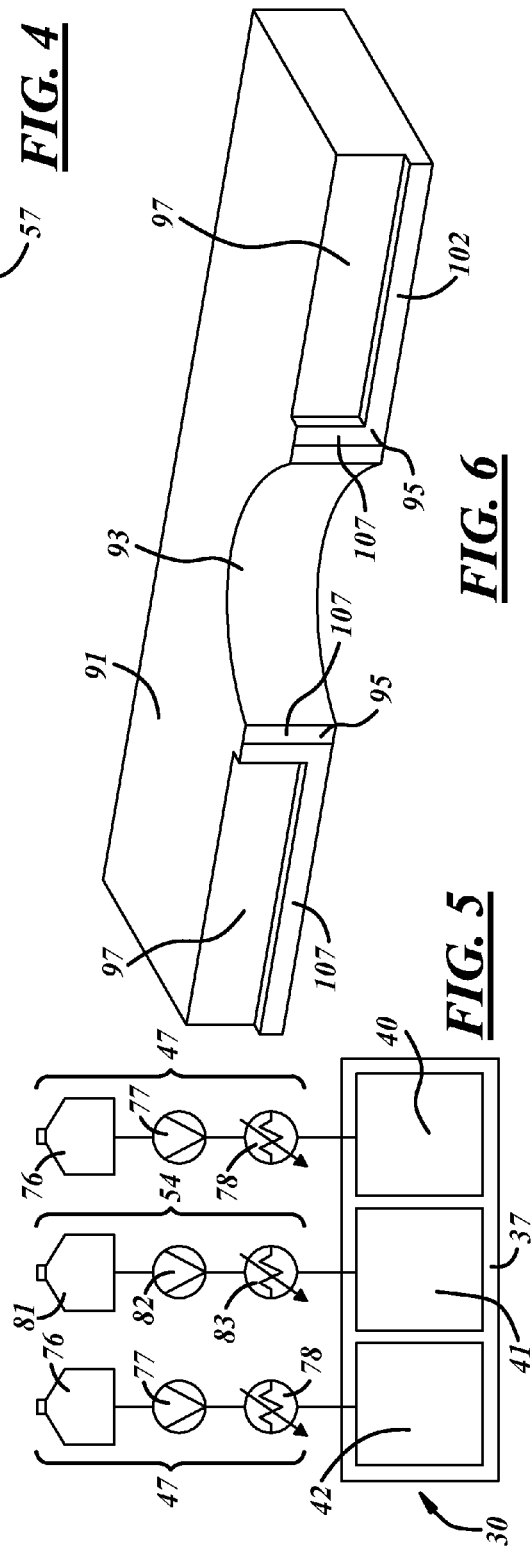

MACHINE FOR FORMING FLEXIBLE POUCHES

CROSS-REFERENCE TO RELATED APPLICATIONS

This application claims priority of U.S. Provisional Patent Application Ser. No. 61/880,363 filed on Sep. 20, 2013, which is incorporated herein by reference.

FIELD OF THE INVENTION

The present invention relates generally to machines for manufacturing a flexible pouch with a fitment. Specifically, to a machine that sterilizes the flexible pouch material, seals the fitment within the pouch, and inspects the fitment installation.

BACKGROUND OF THE INVENTION

Various types of disposable portable containers are known in the art for storing a fluid or dry product such as a liquid, granular material, powder, or the like. Examples of containers include a cup, a metal can, a plastic bottle, a glass bottle, or a flexible pouch. Consumers prefer the convenience of flexible pouches over other types of containers due to their shape, size, shelf life, and storage adaptability. Manufacturers recognize the packaging benefits of a flexible pouch since the pouch can be formed and filled on the same manufacturing line. An example of a method and apparatus for filling a flexible pouch with a product is disclosed in commonly assigned U.S. Pat. No. 6,199,601 which is incorporated herein by reference.

The flexible pouch is made from a flexible film, preferably an extrusion or a laminate composed of sheets of plastic and aluminum or the like. An outer layer of material may include preprinted information such as a logo or the like to provide the customer with information regarding the contents of the pouch.

It is known to produce flexible pouches on form-fill-seal machines. These machines operate at high speed to produce the pouches from a roll of flexible film. The film is first drawn through the machine and folded over a plow to double the material into a sleeve. A gusset is then formed in the bottom. If the contents of the pouch will be food or beverage, the sleeve is passed through a hydrogen peroxide bath to sterilize the film. The sleeve then passes through seal bars which form side edges and shape the gussets. The sleeve is then separated into individual pouches. In some cases a fitment spout and cap is inserted as a unit into the top and sealed or the fitment is mounted and filled through the spout and then the cap is installed. It is important to make sure that the fitment is properly aligned and properly sealed into the pouch to prevent leakage.

SUMMARY OF THE INVENTION

A machine for producing a flexible pouch with a fitment includes a housing. A sterilization chamber apparatus is disposed with the housing. The sterilization chamber apparatus has an entry compartment supplied with oxygen, a center compartment supplied with hydrogen peroxide, and an exit compartment supplied with oxygen. The machine also includes a sealing apparatus having a seal bar disposed within the housing. The seal bar has a center cavity disposed between a pair of sideways L-shaped portions and rectangular recesses. Further disposed within the housing of the machine is a digital photograph inspection apparatus that has a digital camera and electronic control unit. The machine operates by moving flexible laminate material formed into a sleeve through the entry compartment, the center compartment and the exit compartment. Next, a fitment is inserted into the sleeve and the sleeve sealed to form the flexible pouch. The fitment is sealed in place with the seal bar. After the fitment is installed, the fitment installation is inspected with the digital photograph inspection apparatus.

A sterilization chamber apparatus for use in the manufacture of a flexible pouch made of laminate material includes a box having an entry compartment, a center compartment, and an exit compartment. A first tube is at least partially disposed with the entry compartment. The first tube supplies oxygen to the entry compartment from an oxygen supply. A second tube is at least partially disposed within the exit compartment. The second tube supplies oxygen to the exit compartment from the oxygen supply. A third tube is at least partially disposed within the center compartment. The third tube supplies hydrogen peroxide to the center chamber from a hydrogen peroxide supply. Laminate material is moved into the entry compartment supplied with oxygen. The laminate material is then moved through the center compartment supplied with hydrogen peroxide. Afterwards, the laminate material is moved through the exit compartment supplied with oxygen and out of the box, thus sterilizing the laminate material.

A method to sterilize laminate material used to manufacture a flexible pouch includes first providing a laminate material in a sleeve shape. Once the sleeve has been provided, oxygen gas is blown into the sleeve. After oxygen gas has been blown into the sleeve, hydrogen peroxide gas is blown into the sleeve. Finally, after the hydrogen peroxide gas has been blown into the sleeve, oxygen gas is again blown into the sleeve.

Once the sleeve has been sterilized, a flexible pouch can be formed from the sleeve by sealing and cutting the sleeve. A fitment can also be inserted and sealed within an edge of the flexible pouch. To help secure the fitment within the flexible pouch a seal bar is used. The seal bar includes a center cavity disposed between a pair of sideways L-shaped portions and a rectangular recess.

After the fitment is installed into the flexible pouch, it is inspected. A method to inspect the fitment within the flexible pouch includes providing a flexible pouch with a fitment. The fitment includes a canoe body with a top surface. The flexible pouch includes a top edge. A digital photo is taken of the pouch with the fitment. In the photo, the top edge of the pouch and the top surface of the canoe are identified. The identified top edge of the pouch and the identified top surface of the canoe body are compared with a rectangular model of the pouch. The flexible pouch is rejected if the top edge of the pouch is not generally parallel with the top surface of the canoe.

BRIEF DESCRIPTION OF THE DRAWINGS

FIG. 4 shows a top plan view of the sterilization chamber apparatus of FIG. 2 with the top removed;

FIG. 5 shows a schematic view of the sterilization chamber apparatus of FIG. 2;

FIG. 6 shows a perspective view of a seal bar;

DETAILED DESCRIPTION OF THE PREFERRED EMBODIMENTS

With reference now to the figures, an embodiment of the claimed invention is shown and discussed. The improvements include an improved method and apparatus for sterilization, a fitment 27 alignment inspection device, and an improved seal mechanism for the fitment 27. The improvements may be used together on one machine 25 or separately depending on the application.

Figure 1:
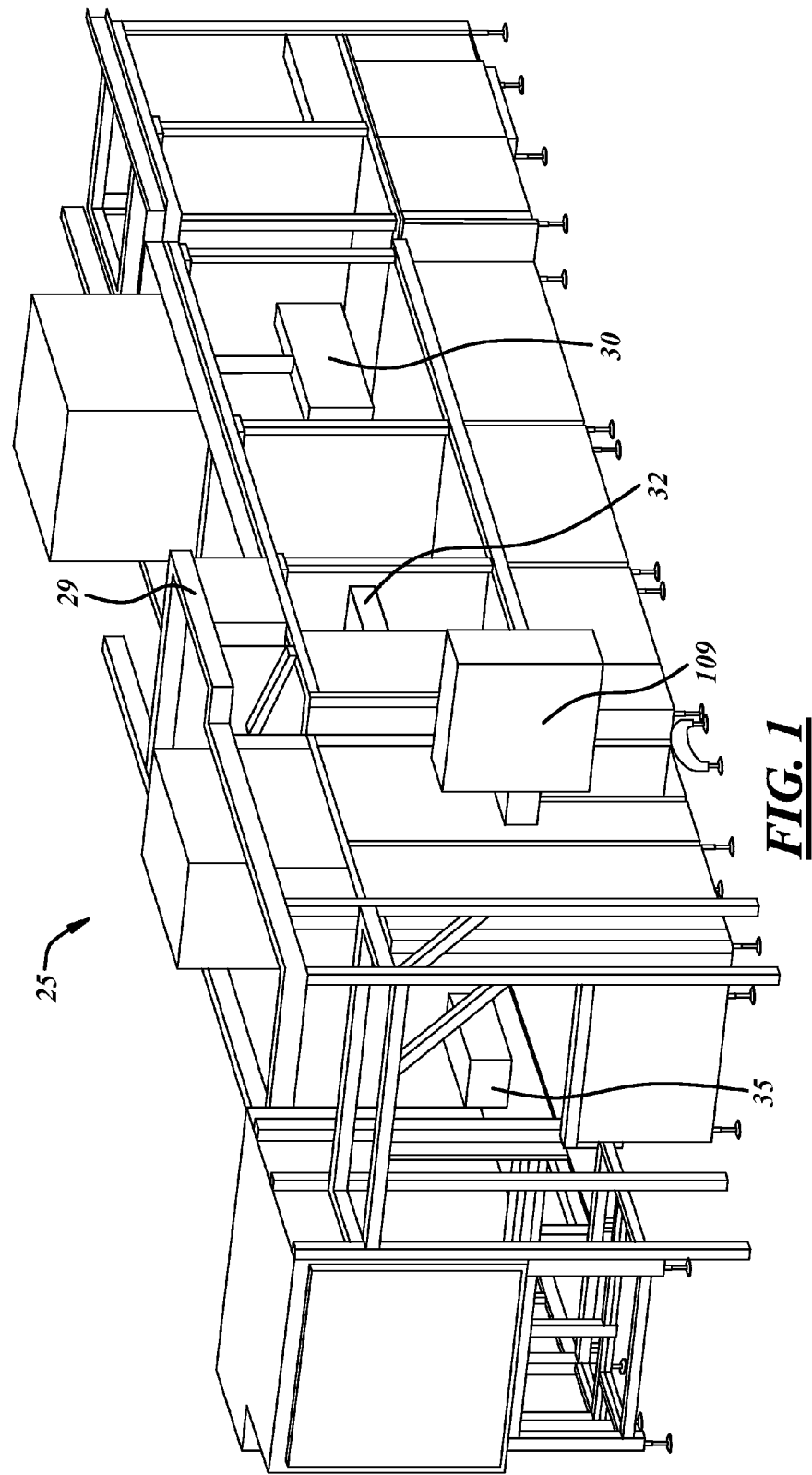
FIG. 1 shows a perspective view of a machine for producing a flexible pouch.
Figure 2:
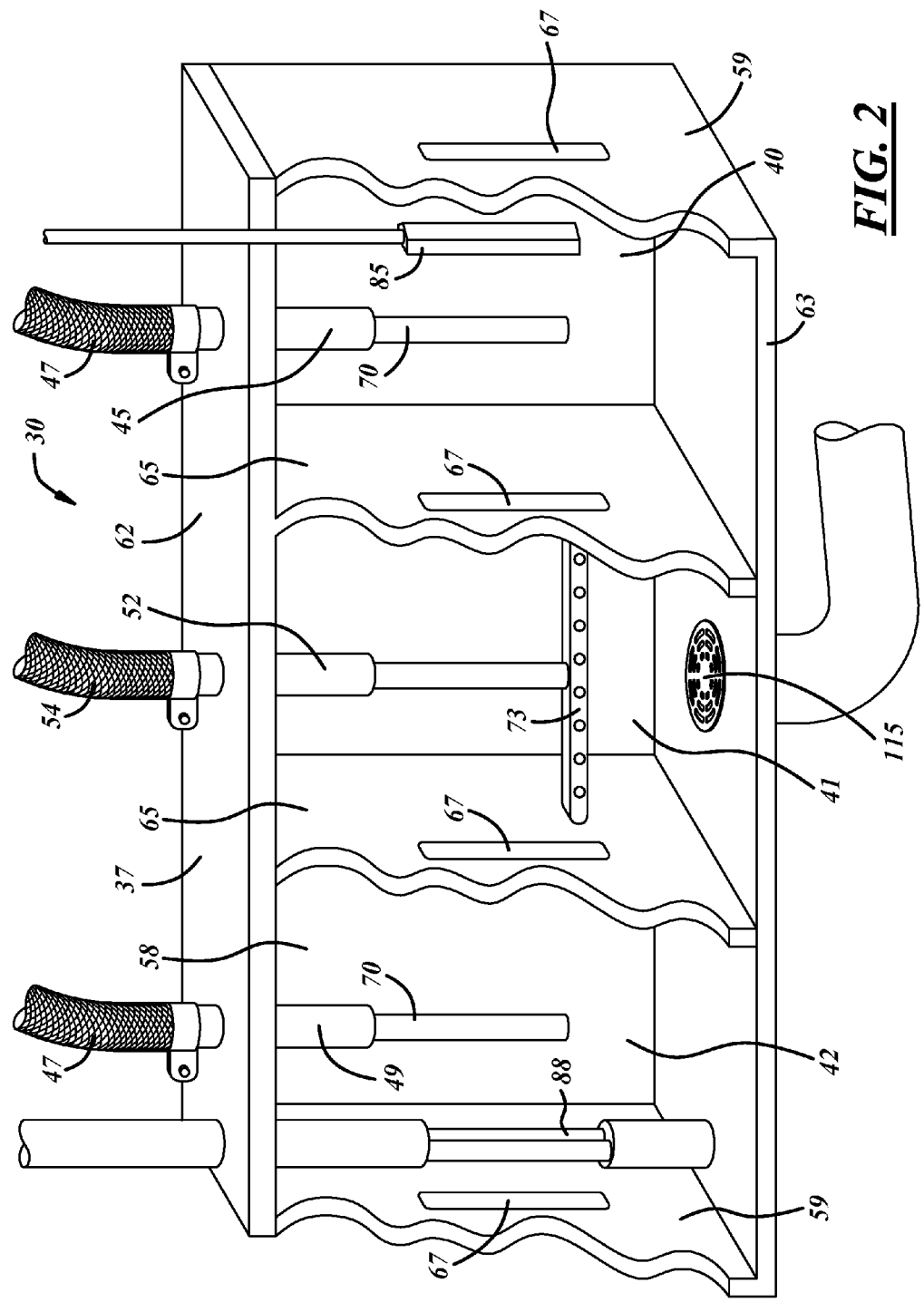
FIG. 2 shows a perspective view of sterilization chamber apparatus with a portion cut away.

As seen in FIG. 1, a fill, form, and seal machine 25 for producing a flexible pouch 26 with a fitment 27 from flexible laminate material 28 is shown. The machine 25 is protected by a housing 29 which covers, at least in part, operational structures of the machine 25. Some of the structures disposed within the housing 29 include a sterilization chamber apparatus 30, a fitment 27 sealing apparatus 32 and a digital photograph inspection apparatus 35.

The sterilization chamber apparatus 30 of the machine 25 can be seen in FIGS. 2-5. The sterilization chamber 30 includes a box 37 having an entry compartment 40, a center compartment 41 and an exit compartment 42. The entry compartment 40 includes a first tube 45 that is at least partially disposed within the entry compartment 40. The first tube 45 supplies oxygen to the entry compartment 40 from an oxygen supply 47. The exit compartment 42 includes a second tube 49 that is at least partially disposed within the exit compartment 42. The second tube 49 supplies oxygen to the exit compartment 42 from the oxygen supply 47. The oxygen supply 47 may be a common supply for both the first and second tube 49. Alternatively, the first tube 45 and second tube 49 could have their own individual oxygen supply 47. The center compartment 41 includes a third tube 52 that is at least partially disposed within the center compartment 41. The third tube 52 supplies hydrogen peroxide (H2O2) to the center compartment 41 from a hydrogen peroxide supply 54.

Laminate material is moved though the entry compartment 40, the center compartment 41, and the exit compartment 42 to be sterilized. In the entry compartment 40 and the exit compartment 42, the oxygen forms a barrier to prevent hydrogen peroxide from escaping the center compartment 41. Hydrogen peroxide escaping from the center compartment 41 will mix with the oxygen in the entry compartment 40 or exit compartment 42 to form water.

The box 37 is formed by a front wall 57, a rear wall 58, and end walls 59. The walls 57, 58, 59 may be formed of a suitable clear material such as Plexiglas. The box 37 is additionally formed by a top wall 62 and a bottom wall 63 which may be constructed out of metal or other suitable material. The center compartment 41 is separated from the entry compartment 40 and exit compartment 42 by two interior walls 65. The entry compartment 40 is formed by one end wall 59 and one interior wall 65. The exit compartment 42 is formed between the other interior wall 65 and other end wall 59. The end walls 59 and interior walls 65 have slits 67 through which the laminate material is passed into and out of the compartments 40, 41, 42 when the machine 25 is in operation.

An oxygen diffuser 70 is mounted to the first tube 45 and second tube 49 within the entry compartment 40 and the exit compartment 42. The oxygen diffuser 70 extends vertically in the entry compartment 40 and the exit compartment 42.

A hydrogen peroxide diffuser 73 is mounted to the third tube 52 within the center compartment 41. The hydrogen peroxide diffuser 73 is an elongated tube having a plurality of openings. The hydrogen peroxide diffuser 73 is suspended by the third tube 52 attached to the top of the center compartment 41. The hydrogen peroxide diffuser 73 is aligned horizontally, or parallel to a direction of movement of the laminate material, within the center compartment 41 when in operation.

The oxygen supply 47 includes an oxygen tank 76, an oxygen pump 77, and an oxygen heater 78. The oxygen is delivered from the oxygen tank 76 by the oxygen pump 77 through the oxygen heater which heats the hydrogen peroxide to 50° centigrade. The oxygen is then pumped by the oxygen pump 77 through a hose to the first tube 45 and second tube 49 at a pressure greater than that of ambient air.

The hydrogen peroxide supply 54 includes a hydrogen peroxide tank 81, a hydrogen peroxide pump 82 and a hydrogen peroxide heater 83. The hydrogen peroxide is delivered from the hydrogen peroxide tank 81 by the hydrogen peroxide pump 82 through the hydrogen peroxide heater 83 which heats the hydrogen peroxide to 70° centigrade. The hydrogen peroxide is then pumped through a hose to the third tube 52 and hydrogen peroxide diffuser 73 at a pressure greater than that of the pumped oxygen. Heating of the hydrogen peroxide and oxygen promotes the interaction there-between to form water, as discussed above.

An opening finger 85 is mounted to extend downwardly from the top of the entry compartment 40. The finger 85 has a sufficient diameter, or width, to separate laminate material in the box 37 as discussed below. The sufficient diameter, or width, of the opening finger 85 can be determined by comparison to the width of the oxygen diffuser 70 and the hydrogen peroxide diffuser 73. The width of the oxygen diffuser 70 and the hydrogen peroxide diffuser 73 are measured in a perpendicular direction as compared to the direction of travel of the flexible laminate material in the box 37. The width or diameter of the opening finger 85 is equal to or greater than the width of the oxygen diffuser 70 and the hydrogen peroxide diffuser 73. The opening finger 85 can be made of plastic, metal, or other suitable material.

A pair of rollers 88 is mounted to extend downwardly from the top of the exit compartment 42. The rollers 88 are positioned close enough together to bring the laminate material previously separated by the opening finger 85 back together. Each roller 88 rotates about an axis that is generally vertical within the box 37. The rollers 88 apply force to the laminate material to bring the material back together while minimizing resistance to the laminate material in the direction the material travels within the box 37. The rollers 88 can be made of plastic, metal or other suitable material.

Figure 7:
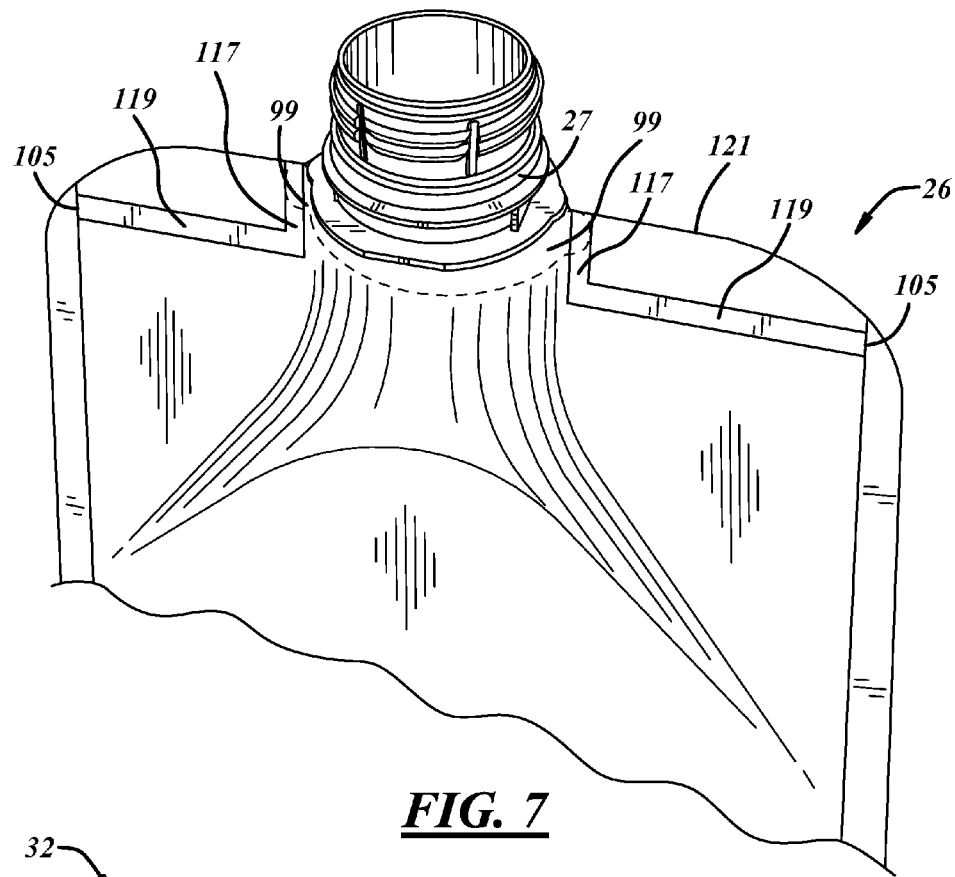
FIG. 7 shows a perspective view of a top portion of a flexible pouch with a fitment.
Figure 8:
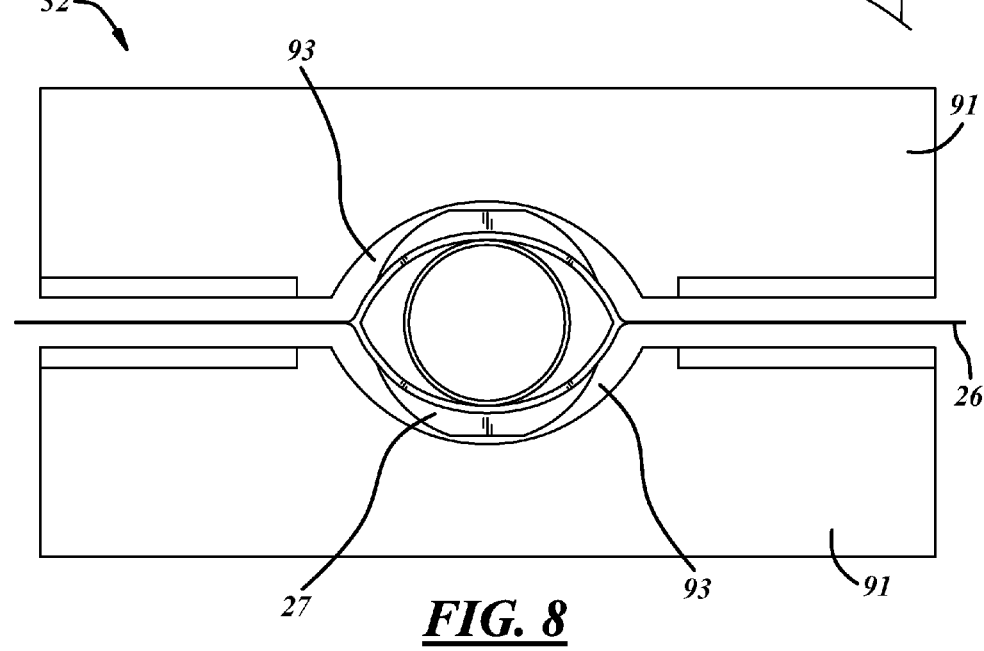
FIG. 8 shows a top plan view of a pair of seal bars used in a fitment sealing apparatus.
Figure 9:
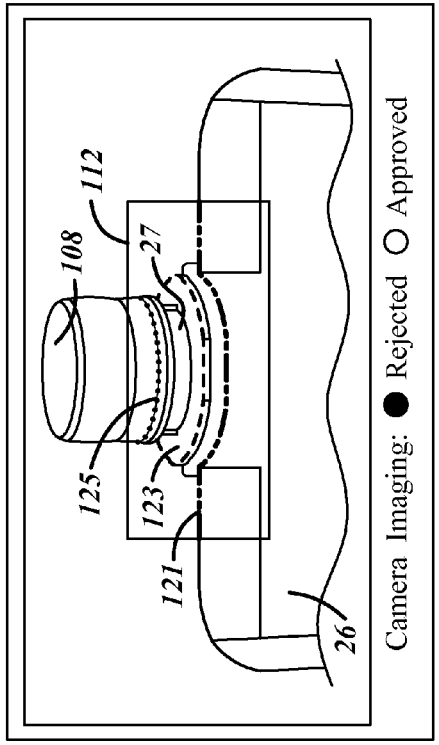
FIG. 9 shows a view of a digital inspection photograph of a pouch with a too deep fitment.
Figure 11:
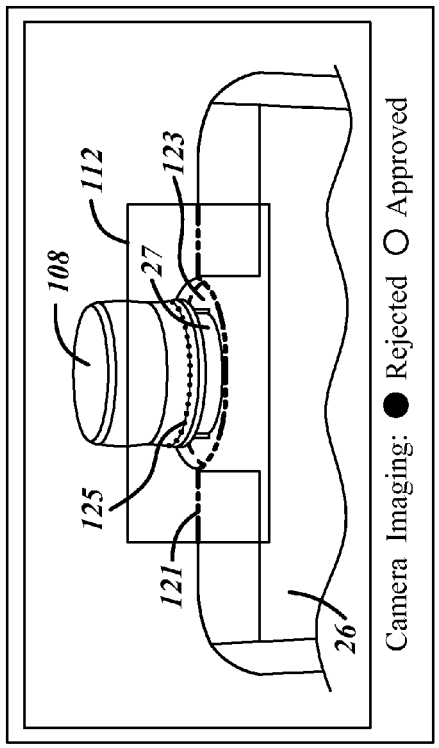
FIG. 11 shows a view of a digital inspection photograph of a pouch with a misaligned fitment.
Figure 10:
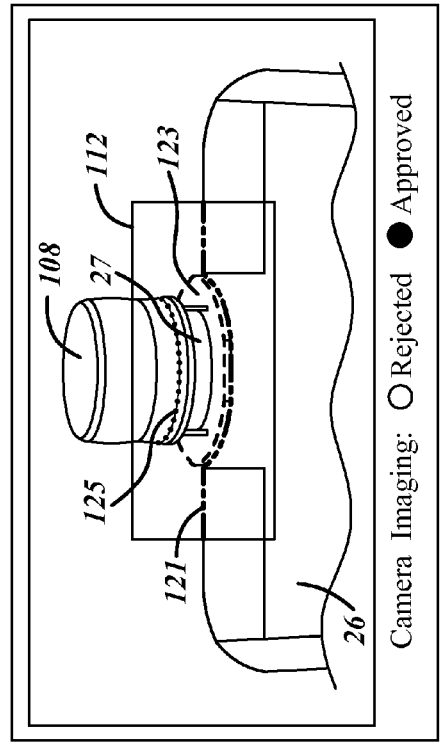
FIG. 10 shows a view of a digital inspection photograph of a pouch with a too high fitment.
Figure 12:
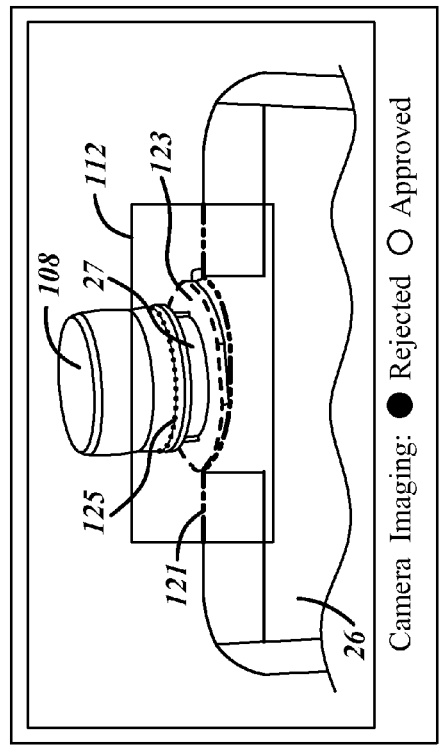
FIG. 12 shows a view of a digital inspection photograph of a pouch with a properly installed fitment.
Figure 13:
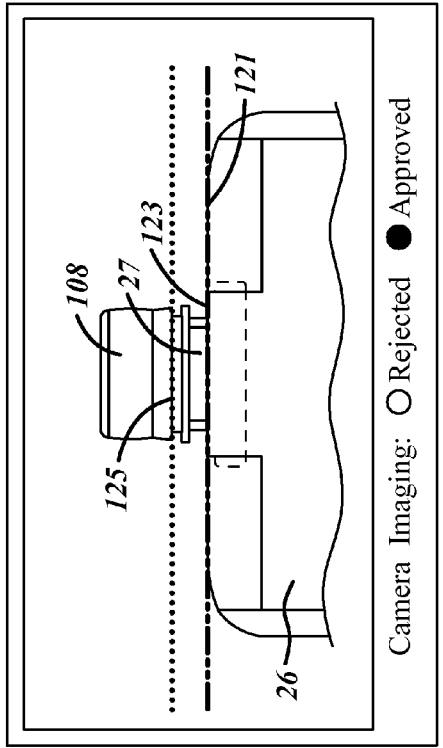
FIG. 13 shows a view of a digital inspection photograph of a pouch with a misaligned fitment.
Figure 14:
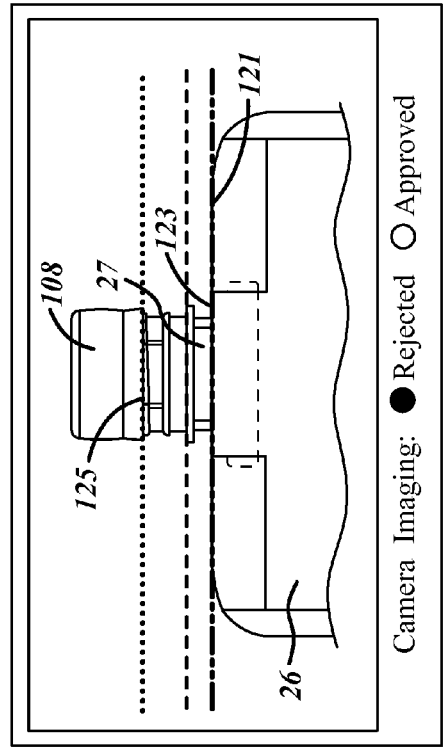
FIG. 14 shows a view of a digital inspection photograph of a pouch with a properly installed fitment.
Figure 15:
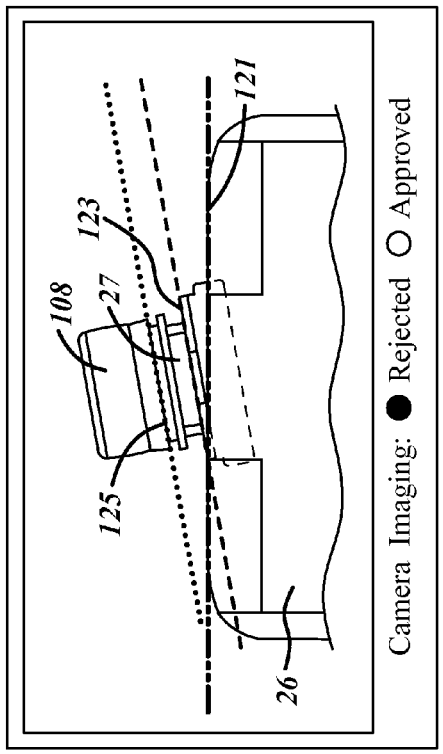
FIG. 15 shows a view of a digital inspection photograph of a pouch with a too high fitment.
Figure 16:
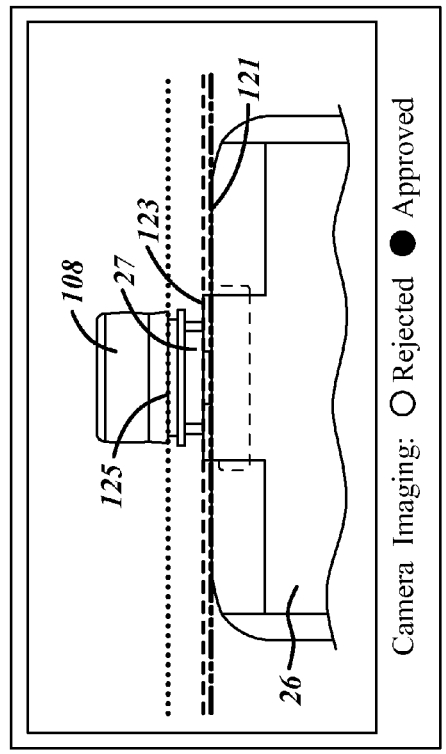
FIG. 16 shows a view of a digital inspection photograph of a pouch with a too high fitment and an untightened cap.

The fitment 27 sealing apparatus 32 includes a seal bar 91 for securing the fitment 27 within the pouch 26, as shown in FIGS. 6-8. The fitment 27 sealing apparatus uses a pair of opposing seal bars 91 that sandwich the flexible pouch 26 and fitment 27 to provide a robust and secure seal of the fitment 27 within the pouch 26.

The seal bar 91 has a center cavity 93 disposed between a pair of sideways L-shaped portions 95 and recesses 97. The center cavity 93 is dimensioned and formed to seal the pouch 26 against a canoe body 99 of the fitment 27. The sideways L-shaped portion 95 has a long horizontal portion 102 which is dimensioned to extend from a side edge 105 of the pouch 26 to abut the canoe 99. The sideways L-shape portion 95 also includes a second portion 107 which extends vertically along the edge of the canoe 99. The rectangular recess 97 of the seal bar 91 are located above the horizontal portion 102 of the "L" 95.

Figure 3:
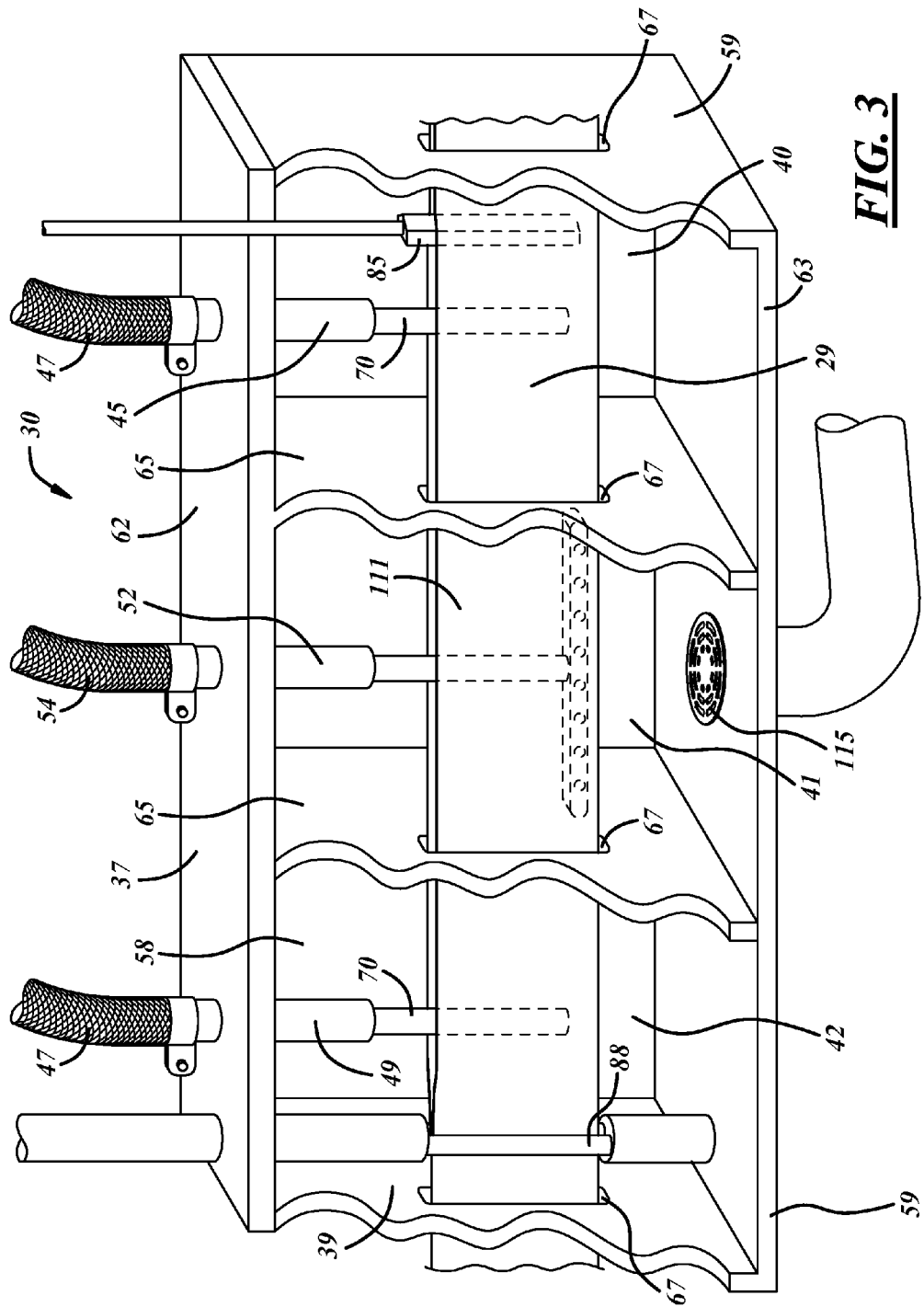
FIG. 3 shows a perspective view of the sterilization chamber apparatus of FIG. 2 with laminate material.
Figure 17:
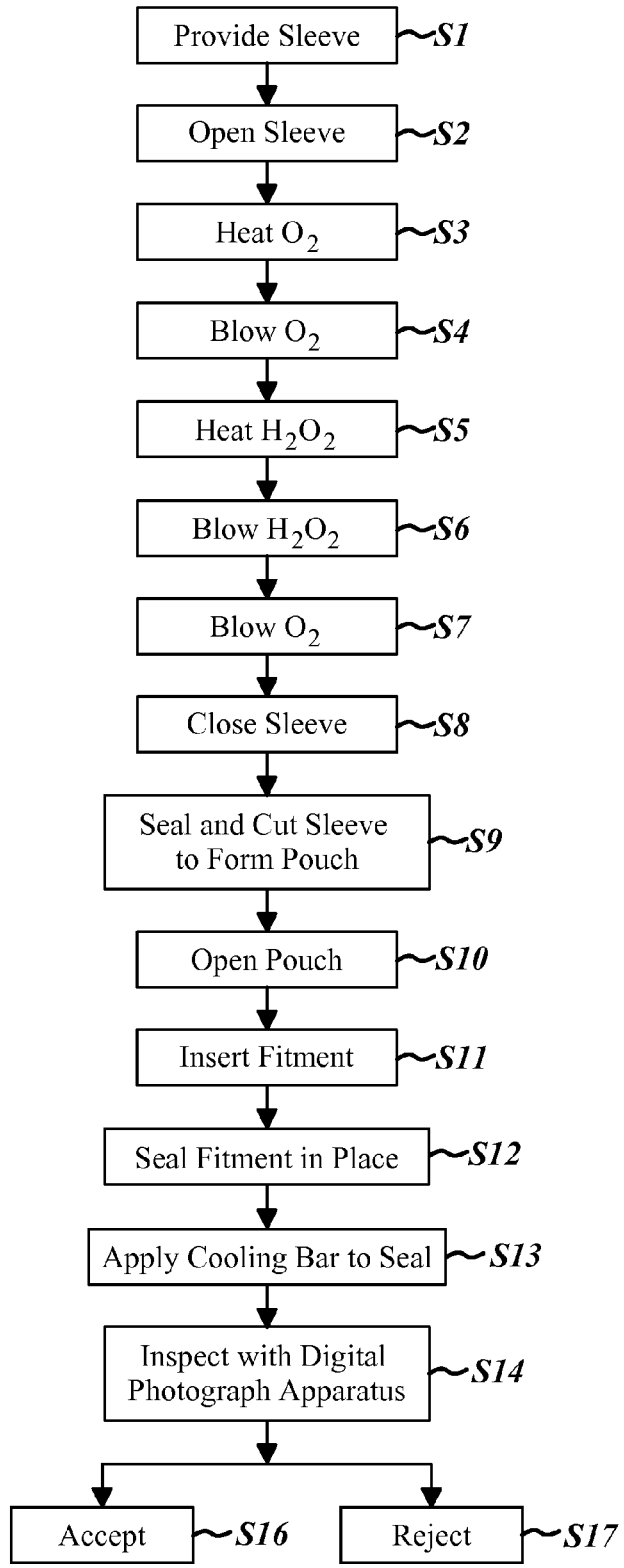
FIG. 17 shows a flowchart of a method for sterilizing, making, and inspecting a flexible pouch with a fitment.

When the machine 25 is operated, a method of sterilizing, forming, and inspecting flexible pouch 26 with a fitment 27 is performed, as laid out by the flow chart in FIG. 17. First a laminate film 29 from a roll is pulled over a plow 110 to fold the film into a sleeve 111 having a U shape, thereby providing the sleeve 111 at step S1. A gusset is formed in the bottom by a fixture which folds the bottom of the sleeve 111 into a "W shape". The sleeve 111 is then guided by rollers into the entry compartment 40 as shown in FIG. 3. The ends have slits 67 formed to receive the sleeve 111 into and out of the chamber. The slits 67 are slightly larger than the sleeve 111.

Then opening finger 85 is mounted to extend downwardly from the top of the entry compartment 40 to slightly above the gusset portion of the sleeve 111. The finger 85 has sufficient diameter to separate the sides of the sleeve 111, thereby opening the sleeve at step S2. A diffusing tube extends into the sleeve 111 upstream of the finger 85 to blow dry oxygen that was heated to about 50 degrees centigrade into the interior of the sleeve 111, steps S3 and S4. The slit 67 on the interior wall 65 of the entry compartment 40 has an opening large enough to permit the sleeve 111, as separated by the finger 85, to pass through the slit 67 in an open position to the center compartment 41.

Within the center compartment 41 the hydrogen peroxide diffuser 73 extends into the sleeve 111 to blow hydrogen peroxide that was heated to about 70 degrees centigrade gas directly into the interior of the sleeve 111 and against the bottom gusset, steps S5 and S6. The H2O2 moves upwardly from the sleeve 111 around the exterior of the sleeve 111 and over the bottom of the gusset thus sterilizing both the inner and outer sides of the sleeve 111 and gusset. An exhaust pipe 115 is mounted to the bottom of the center compartment 41 to draw out the H2O2 gas. The sleeve 111 then passes into the exit compartment 42 through the interior wall 65 of the exit compartment 42 which has a slot dimensioned to receive the sleeve 111 in an open state.

Within the exit compartment 42, the second tube 49 for supplying oxygen extends downwardly from the top to blow oxygen from the heater at 50° centigrade into the sleeve 111, step S7. The oxygen is blown into the sleeve 111 to block any hydrogen peroxide which passes from the center compartment 41 into the exit compartment 42. The sleeve 111 then is passed through a pair of rollers 88 extending downwardly in the exit compartment 42 to close the sterilized sleeve 111, step S8. The sleeve 111 is drawn out of the exit compartment 42 through a slit 67 in the exterior wall of the exit compartment 42.

The sleeve 111 is then passed to a station with a heat seal bar which begins the formation of the pouch 26 by placing a tack seal at the bottom corner of every other pouch 26. The tack seal is placed to hold the pouch 26 and gusset in a closed position as the sleeve passes further downstream to a station where the side seal is formed with a heat bar and then to a cutting station where the pouches 26 are separated by a knife from each other, step S9. The pouches 26 are then grabbed by grippers and moved to a station where the pouches 26 are opened, step S10. The pouch 26 is then moved to a station where a fitment 27 having a cap 108 is positioned in the top of the pouch 26, step S11. The fitment 27 is delivered from a bowl feeder through a sterilization chamber having hydrogen peroxide. The pouch 26 is moved to a station where a seal bar tack seals the front and back panels to the canoe body 99 and then the pouch 26 with fitment 27 is moved to a station the seal bar 91 forms a second seal over the top edge 121 of the pouch 26 and canoe body 99 of the fitment 27, step S12. The second seal is done at a higher temperature (250° C.) and pressure. The seal bar 91 used at the higher temperature and pressure has a center cavity 93 between the pair of sideways "L" shaped portions and rectangular recesses, as described above. As shown in FIGS. 6-8, the sideways "L" seal creates a deep sideways "L" in the pouch 26 which has a vertical portion 117 which extends into the distal edge of the canoe 99 and a horizontal portion 119 extending from the canoe to the side edge of the pouch 26. The pouch 26 thus formed results in an inverted L shaped groove formed in the pouch 26 which forms a very tight seal barrier between the contents of the pouch 26 and the side edge of the canoe 99 to prevent any separation and leakage occurring from or in the pouch 26 particularly at the juncture of flexible laminate material and canoe 99. The pouches 26 are then moved to a station where a cooling bar is applied at a temperature of 140° C. to the seal, step S13.

The pouch 26 then is moved to a fill station where the cap 108 is removed and the pouch 26 is filled through the spout of the fitment 27. After the pouch 26 is filled, it is then moved to a capping station where a robotic arm screws the cap 108 to the proper position. The pouch 26 is then moved to the digital photograph inspection apparatus 35 where a digital camera takes a photograph of a portion of the pouch and fitment. The photograph is received by a comparing module, or electronic control unit configured to run recognition software. As further described below, recognition software is used to recognize the top edge 121 of the pouch 26, the top surface 123 of the canoe body 99, and the lower edge 125 of the cap 108. The lines are then compared to a stored rectangular model of the pouch 26 and cap 108, or to each other, to determine whether the top of the canoe 99 is properly aligned with the top edge 121 of the pouch 26 and the cap 108 is properly tightened on the spout by checking the gap between the bottom of the cap 108 and the top of the canoe body 99, step S14. If the canoe is not aligned horizontally or flush with the top edge 121 of the pouch 26, the pouch 26 is rejected and a signal is sent to a discharge station where the pouch 26 is dropped into rejected passage and sent to scrap, S15. If the pouch, fitment, and cap are proper, the assembly is accepted and sent to be packaged for shipment, step S16.

To inspect the installation of the fitment 27 within the pouch 26 at step S14, and the installation of a cap 108 to the fitment 27 the video inspection device 35 is used. The video inspection device 35 includes a digital camera in communication with an electronic control unit. The digital camera takes a digital photograph of at least a portion of the flexible pouch 26, fitment 27 and cap 108. The digital photograph is sent to the electronic control unit for processing. The video inspection device 35 can additionally include a monitor 109 to allow an operator of the machine 25 to view the photographs taken by the digital camera.

The electronic control unit is configured to isolate a portion 112, or box, within the digital photograph and identify features within the portion 112. The identification is typically done by way of contrast comparison. A border line between areas of different contrast, color, texture, etc., is identified. The shape and location of the identified border lines are compared to model lines, or other parameters, in the electronic control unit, thereby allowing the electronic control unit to identify a top edge 121 of the pouch 26, a top surface 123 of the canoe portion of the fitment 27, a bottom edge 125 of the cap 108 secured to the fitment 27, etc.

Depending on the camera angle taking the photograph of the pouch 26, different lines can be identified. For example, as illustrated in FIGS. 9-12, the photograph can be taken from a top front perspective view. In the top front perspective view, the top edge 121 of the flexible pouch 26 may be identified by border lines having an arcuate portion near the center of the isolated portion connected with generally straight and horizontal portions near the sides of the isolated portion (as shown by the alternated long-short dashed lines in FIGS. 9-12). The top surface 123 of the fitment 27 may be identified as a borderline with an arcuate shape near the center of the isolated portion (as shown by the dashed lines in FIGS. 9-12). The bottom edge 125 of the cap 108 may be identified as a border line with an arcuate shape near the center of the isolated area above the identified top edge 121 of the pouch 26 and/or the identified top surface 123 of the canoe (as shown by the dotted line in FIGS. 9-12). In situations where the top surface 123 of the canoe is located above the top edge 121 of the pouch 26, the center arcuate portion of the top edge 121 will not be visible, and the top edge 121 of the pouch 26 identified will be identified by the generally straight and horizontal portions near the sides of the isolated portion. In situations where the top surface 123 of the canoe cannot be distinguished from the arcuate portion of the top edge 121 of the pouch 26, such as when they are flush with each other, the electronic control unit will identify both as being located in the same location.

The photograph may also be taken from a front elevation view, as illustrated in FIGS. 13-16. In the front elevation view, the top edge 121 of the pouch 26, the top surface 123 of the canoe, and bottom edge 125 of the cap 108 are all straight border lines. The electronic control unit distinguishes between the lines based on their length and location relative to each other. The bottom edge 125 of the cap 108 is the top most identification line (shown by the dotted line in FIGS. 13-16). The top edge 121 of the pouch 26 is the bottom most identification line (shown by the alternating short-long dashed line in FIG. 13-16). The top surface 123 of the fitment 27 (shown by the dashed line in FIGS. 13-16) is located between the bottom edge 125 of the cap 108 and the top edge 121 of the pouch 26.

When analyzing the lines to inspect the fitment 27, the angle/orientation and location of one line relative to another line is considered. For example, in the top perspective view, when the arcuate portion of the top edge 121 of the pouch 26 and the arcuate portion of the top surface 123 of the canoe are either spaced apart by an equidistance along their length, or identically overlap along their length, the electronic control unit can determine that the fitment 27 is properly aligned within the pouch 26. When the spacing between the arcuate portion of the top edge 121 of the pouch 26 and the arcuate portion of the top surface 123 of the canoe increases/decreases from right to left, or vise versa, then the electronic control unit can determine that fitment 27 is improperly aligned within the pouch 26.

The electronic control unit may also determine when the fitment 27 is located in a proper vertical position within the pouch 26. For example, when the vertical distance between the top edge 121 of the pouch 26 and the arcuate portion of the top surface 123 of the canoe is higher than a predetermined amount, or outside a tolerance level, the fitment 27 is determined to not be in a proper location.

Additionally, the electronic control unit may be configured to determine when the cap 108 is properly installed. For example, the vertical distance between the identified border lines representing the top surface 123 of the canoe and bottom edge 125 of the cap 108 is determined by the electronic control unit. When the distance between the top surface 123 of the canoe and bottom edge 125 of the cap 108 is above a threshold amount, or outside of a tolerance level, the electronic control unit determines that the cap 108 is not properly installed, for example when a thread on type cap 108 has not been fully tightened.

The invention is not restricted to the illustrative examples described above. Examples described are not intended to limit the scope of the invention. Changes therein, other combinations of elements, and other applications will occur to those skilled in the art without deviating from the spirit of the described invention.

The invention claimed is:

1. A machine for producing a flexible pouch with a fitment comprising:
   a housing;
   a sterilization chamber apparatus disposed within the housing, the sterilization chamber apparatus includes a box having an entry compartment supplied with oxygen, a center compartment supplied with hydrogen peroxide and an exit compartment supplied with oxygen;
   a fitment sealing apparatus disposed within the housing, the fitment sealing apparatus includes a seal bar having a center cavity disposed between a pair of sideways L-shaped portions and rectangular recesses; and
   a digital photograph inspection apparatus disposed within the housing, the digital photograph inspection apparatus includes a digital camera in communication with an electronic control unit;
   wherein a laminate material is folded to form a sleeve for forming the flexible pouch, the sleeve is moved through the entry compartment, the center compartment and the exit compartment for sterilization, the fitment is installed and sealed into the sleeve with the seal bar, and the installation of the fitment is inspected by the digital photograph inspection apparatus.

2. The machine for producing a flexible pouch of claim 1 further comprising:
   a first tube for supplying oxygen from an oxygen supply, the first tube at least partially disposed within the entry compartment;
   a second tube for supplying oxygen from the oxygen supply, the second tube at least partially disposed within the exit compartment;
   a third tube for supplying hydrogen peroxide from a hydrogen peroxide supply, the third tube at least partially disposed within the center compartment; and a diffuser mounted to the end of the third tube, the diffuser aligned horizontally within the center compartment.

3. A sterilization chamber apparatus for use in the manufacture of a flexible pouch made of a laminate material comprising:
   a source of oxygen;
   a source of hydrogen peroxide;
   a box having an entry compartment, a center compartment and an exit compartment;
   a first tube for supplying oxygen from the source of oxygen, the first tube at least partially disposed within the entry compartment;
   a second tube for supplying oxygen from the source of oxygen, the second tube at least partially disposed within the exit compartment;
   a third tube for supplying hydrogen peroxide from the source of hydrogen peroxide, the third tube at least partially tube disposed within the center compartment;
   wherein the entry and exit compartment are supplied with oxygen from first and second tubes, the center compartment is supplied with hydrogen peroxide from the third tube, and the laminate material is moved into the entry compartment, through the center compartment and out the exit compartment to sterilize the laminate material.

4. The sterilization chamber apparatus of claim 3 further comprising:
   a diffuser mounted to the end of the third tube, the diffuser aligned horizontally within the center compartment.

5. The sterilization chamber apparatus of claim 4 further comprising:
   a first heater attached to the first and second tubes, the first heater capable of warming the oxygen supplied by the first and second tubes to a temperature of 50 degrees centigrade;
   a first pump attached to the first and second tubes, the pump capable of pumping oxygen at a pressure greater than ambient air.

6. The sterilization chamber apparatus of claim 5 further comprising:
   a second heater attached to the third tube, the second heater capable of warming the hydrogen peroxide supplied by the third tube to a temperature of 70 degrees centigrade;
   a second pump attached to the third tube, the second pump capable of pumping hydrogen peroxide at a pressure greater than the oxygen pumped by the first pump.

7. An apparatus to seal a fitment within a flexible pouch comprising:
   a seal bar having a center cavity disposed between a pair of sideways L-shaped portions and rectangular recesses.

8. The apparatus of claim 7 wherein the sideways L-shaped portion has a predetermined height and width, the predetermined height of sideways L-shaped portion is determined based on a height of a canoe portion of the fitment to be sealed in the flexible pouch, and the width of the sideways L-shaped portion is determined based on the width of the flexible pouch.

\* \* \* \* \*